(12) United States Patent
Magana et al.

(10) Patent No.: US 9,737,361 B2
(45) Date of Patent: Aug. 22, 2017

(54) SYSTEM AND METHOD FOR A CATHETER

(71) Applicant: ABBOTT CARDIOVASCULAR SYSTEMS INC., Santa Clara, CA (US)

(72) Inventors: Jesus Magana, Redwood City, CA (US); John Stankus, Campbell, CA (US); Benny Serna, Gilroy, CA (US); Michael Ngo, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 329 days.

(21) Appl. No.: 14/574,664

(22) Filed: Dec. 18, 2014

(65) Prior Publication Data

US 2016/0175040 A1    Jun. 23, 2016

(51) Int. Cl.
*A61B 18/14* (2006.01)
*A61B 18/00* (2006.01)
*A61M 25/04* (2006.01)
*A61B 17/00* (2006.01)

(52) U.S. Cl.
CPC ...... *A61B 18/1492* (2013.01); *A61B 2017/00526* (2013.01); *A61B 2018/00404* (2013.01); *A61B 2018/00434* (2013.01); *A61B 2018/00511* (2013.01); *A61B 2018/00577* (2013.01); *A61B 2018/1435* (2013.01); *A61M 25/04* (2013.01)

(58) Field of Classification Search
CPC .......................................... A61B 2018/00511
USPC ...................................................... 606/33, 34
See application file for complete search history.

(56) References Cited

U.S. PATENT DOCUMENTS

| | | | |
|---|---|---|---|
| 2005/0143770 A1* | 6/2005 | Carter | A61B 1/018 606/170 |
| 2006/0079787 A1* | 4/2006 | Whiting | A61M 25/0041 600/466 |
| 2008/0108987 A1* | 5/2008 | Bruszewski | A61B 18/1492 606/32 |
| 2012/0053615 A1* | 3/2012 | Adams | A61F 2/013 606/200 |
| 2012/0101561 A1* | 4/2012 | Porter | A61F 2/95 623/1.11 |
| 2012/0116382 A1* | 5/2012 | Ku | A61B 18/1492 606/33 |
| 2012/0116383 A1 | 5/2012 | Mauch | |

(Continued)

*Primary Examiner* — Linda Dvorak
*Assistant Examiner* — Ryan T Clark
(74) *Attorney, Agent, or Firm* — David J. Pitman; Fulwider Patton LLP

(57) ABSTRACT

A catheter apparatus defining a first lumen with a first internal diameter, the catheter apparatus further comprising a shaping structure having a distal end and a proximal end and a length therebetween, the shaping structure being moveable between a delivery state having a first helical shape, and a deployed state having a second helical shape. A deployment member having a second lumen with a second internal diameter, a first portion of the deployment member being positioned within the first lumen and having a third outside diameter sized to enable the deployment member to slide within the first lumen, the deployment member being operably coupled to the distal end of the shaping structure and being configured such that distal axial movement of the deployment member places the shaping structure in the delivery state, and proximal axial movement of the deployment member places the shaping structure in the deployed state.

5 Claims, 13 Drawing Sheets

(56) References Cited

U.S. PATENT DOCUMENTS

| | | | |
|---|---|---|---|
| 2013/0109987 A1* | 5/2013 | Kunis | A61B 18/1492 600/509 |
| 2014/0121641 A1* | 5/2014 | Fischell | A61M 25/0084 604/509 |
| 2014/0276747 A1* | 9/2014 | Abunassar | A61F 7/12 606/33 |
| 2014/0276748 A1* | 9/2014 | Ku | A61B 18/18 606/33 |
| 2014/0276783 A1* | 9/2014 | Srivastava | A61B 18/1492 606/41 |
| 2015/0011834 A1* | 1/2015 | Ayala | A61B 17/0218 600/208 |
| 2015/0230859 A1* | 8/2015 | Mauch | A61B 18/1492 606/41 |
| 2015/0250481 A1* | 9/2015 | Chobotov | A61B 17/12118 623/1.12 |

* cited by examiner

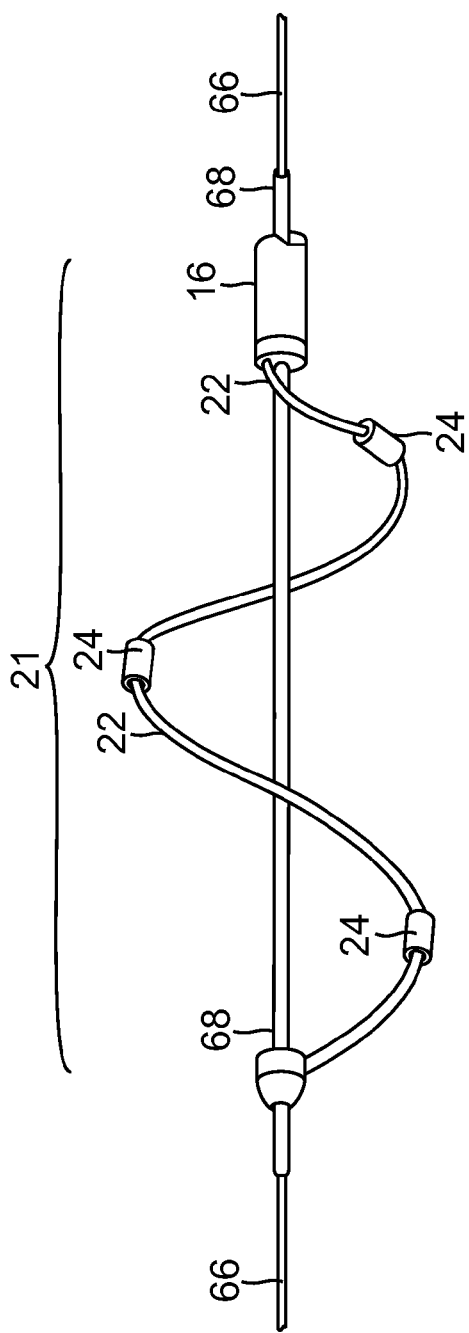
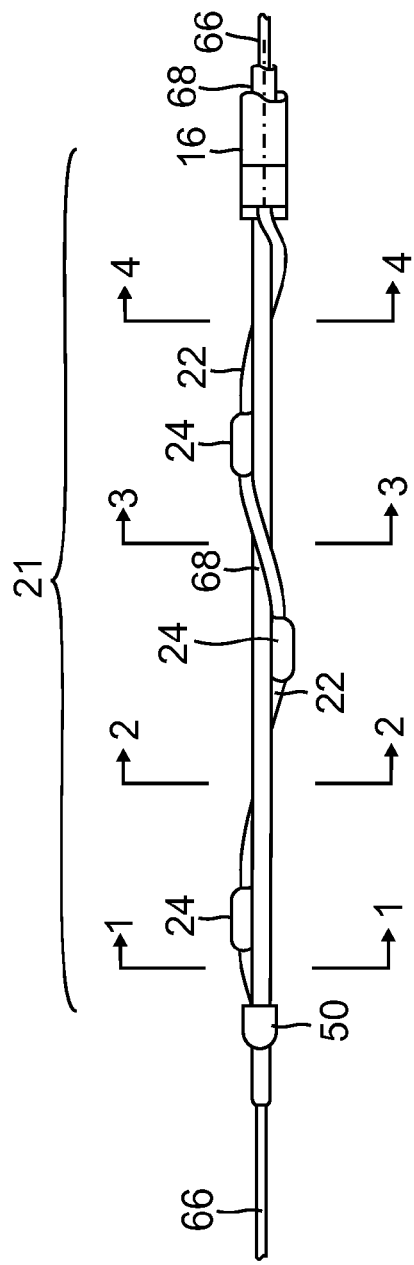
FIG. 4A
FIG. 4B

SYSTEM AND METHOD FOR A CATHETER

BACKGROUND

This invention relates to methods and devices for treatment of diseases that include congestive heart failure, chronic renal failure and hypertension. Specifically, the invention relates to manufacturing a catheter that modulates or blocks signals to the renal nerve of a patient.

Congestive Heart Failure (CHF) is a form of heart disease that is becoming ever more common. The number of patients with CHF is expected to grow in increasing numbers as the so-called "Baby Boomers" reach 50 years of age. CHF is a health condition that occurs when the heart becomes damaged, resulting in a reduced blood flow to the organs of the body. If blood flow decreases sufficiently, kidney function becomes impaired and results in fluid retention, abnormal hormone secretions and increased constriction of blood vessels. These results increase the stress on the heart to do work, and further decrease the capacity of the heart to pump blood through the kidney and vascular circulation system. This reduced capacity further reduces blood flow to the kidney. It is believed that this cycle of reduced kidney perfusion is the principal non-cardiac cause perpetuating a patient's downward spiral into CHF. Moreover, the fluid overload and associated clinical symptoms resulting from these changes are predominant causes for excessive hospital admissions, reduced quality of life and overwhelming costs to the health care system.

While many different diseases may cause initial damage to the heart, once such damage is present, CHF is identifiable under two types: Chronic CHF and Acute CHF. Despite its name, the chronic form is the less acute form of the two but is a longer term, slowly progressive, degenerative disease and may lead to cardiac insufficiency. Chronic CHF is clinically categorized by the patient's mere inability to exercise or perform normal activities of daily living.

By contrast, patients with Acute CHF may experience a more severe deterioration in heart function than those with Chronic CHF. The Acute form results in the inability of the heart to maintain sufficient blood flow and pressure to keep vital organs of the body alive. This condition can occur when extra stress (such as by infection) significantly increases the workload on the heart in a patient with an otherwise stable form of CHF. By contrast to a mere stepwise downward progression that is observable in patients with Chronic CHF, a patient suffering Acute CHF may deteriorate rapidly from even the earliest stages of CHF to severe hemodynamic collapse. Moreover, Acute CHF can occur within hours or days following an Acute Myocardial Infarction (AMI), which is a sudden, irreversible injury to the heart muscle, identified in common parlance as a heart attack.

Against this background, the kidneys are known to play an important regulatory role in maintaining the homeostatic balance of the body. The kidneys eliminate foreign chemicals from the body, regulate inorganic substances, and function as endocrine glands to secrete hormonal substances like renin and erythropoietin. The main functions of the kidney are to maintain the water balance of the body and control metabolic homeostasis by making the urine more or less concentrated, thus either reabsorbing or excreting more fluid. However, when renal disease arises, some otherwise ordinary and regular physiological functions may become detrimental to the patient's health. When this occurs, the process is known as overcompensation. In the case of Chronic Renal Failure (CRF) the event of overcompensation may manifest itself as hypertension that has the effect of damaging the heart and blood vessels, and can eventually result in a stroke or death. Thus, without proper function by the kidneys, a patient may suffer water retention, reduced urine flow, and an accumulation of waste toxins in the blood and body. These conditions resulting from reduced renal function, or renal failure (kidney failure), tend to increase the workload placed upon the heart. In a patient, simultaneous occurrence of both CRF and CHF may cause the heart to further deteriorate as the water build-up and blood toxins accumulate due to the poorly functioning kidneys and may, in turn, cause the heart further harm.

It has been observed, in connection with human kidney transplantation, that there is evidence to suggest that the nervous system plays a major role in kidney function. It was noted for example that after a transplant, when all the renal nerves are severed, the kidney was observed to increase excretion of water and sodium. This phenomenon has also been observed in animals when renal nerves are cut or chemically destroyed. The phenomenon has been termed "denervation diuresis" because the denervation acted on a kidney in a similar way to a diuretic medication. Later, observation of "denervation diuresis" was found to be associated with vasodilatation of the renal arterial system that led to the increase of the blood flow through the kidney. This observation was confirmed by the further observation in animals that reducing blood pressure supplying the kidney could reverse the "denervation diuresis".

It was also observed that after several months passed after kidney transplant surgery in successful cases, the "denervation diuresis" in transplant recipients stopped, and the kidney function returned to normal. Initially, it was believed that "renal diuresis" is merely a passing phenomenon and that the nerves conducting signals from the central nervous system to the kidney are not essential for kidney function. Later discoveries led to the present generally held conclusion that the renal nerves have an ability to regenerate, and that the reversal of the "denervation diuresis" is attributable to the growth of the new nerve fibers supplying kidneys with the necessary stimuli.

In summary then, it is known from clinical experience and also from the existing large body of animal research that stimulation of the renal nerve leads to the vasoconstriction of blood vessels supplying the kidney, decreased renal blood flow, decreased removal of water and sodium from the body and increased renin secretion. It is also known that reduction of the sympathetic renal nerve activity, achieved by renal denervation, can beneficially reverse these processes.

There has therefore already been identified a need in the art for methods and devices that may apply the observed effects set forth above to halt and reverse the symptoms of Congestive Heart Failure. Thus, certain methods and devices have already been developed in the art to reduce renal nerve activity, in order to meet the aforesaid need. For example, the following patents and applications are directed to the stated need: U.S. Pat. No. 8,347,891, and U.S. Application 2012/0143293, which are incorporated herein by reference. In some approaches configured to induce selective damage to the renal nerves (renal denervation), manufacturers have developed and used radio frequency (RF) catheters, which, while being minimally invasive, have problems related to positioning electrodes within a vessel, and maintaining uniform contact between the electrodes and the vessel wall. For example, in certain systems for denervation, treatment assemblies are used which comprise a helical shaping structure for supporting a plurality of electrodes which are deployed to place the electrodes in contact with a vessel wall. Experience of using these systems reveals that problems arise when inserting a catheter into the vasculature of a patient. Specifically, catheters inserted "over the wire" create a problem for a surgeon in that he may be obliged to stand back from the patient by a distance equal to the length of the catheter. Attempts to fashion a catheter as a "rapid exchange" catheter result in a catheter that has an entrance opening that gives the catheter too large an outside diameter; or a catheter in which the distal tip is not sufficiently flexible as a result of the entrance opening being positioned in the distal tip.

Thus, there is a need in the medical arts to produce a system and method for RF-based renal therapy which has a reduced outside diameter, and which retains a soft distal tip. The present invention addresses these and other needs

SUMMARY OF THE INVENTION

In some embodiments, the invention is a catheter apparatus for treatment of a human patient. The apparatus comprises an elongate shaft defining a first lumen with a first internal diameter. A shaping structure having a distal end and a proximal end and a length therebetween is provided, the shaping structure being moveable between a delivery state having a first helical shape, and a deployed state having a second helical shape. At least one electrode is carried by the shaping structure. A deployment member is provided, having a second lumen, a first portion of the deployment member being positioned within the first lumen and having a second external diameter sized to enable the deployment member to slide within the first lumen. The deployment member is coupled to the distal end of the shaping structure and is configured such that distal axial movement of the deployment member places the shaping structure in the delivery state, and proximal axial movement of the deployment member places the shaping structure in the deployed state. A second portion of the deployment member is positioned outside the first lumen and defines a port configured to extend between the second lumen and an exterior surface of the deployment member. In some embodiments, the second lumen is blocked proximal to the port. In further embodiments, a guidewire extends along the second lumen from a distal end of the deployment member, the guidewire emerging from the second lumen to the exterior surface of the deployment member via the port. In yet further embodiments, the deployment member includes reinforcing material around the port, the reinforcing material having a third external diameter that is larger than the first internal diameter, whereby the reinforcing material cannot slide within the first lumen. In some embodiments, a stiffening mandrel is located within the deployment member, the stiffening mandrel extending from a location proximal of the port to a location distal of the port. The stiffening mandrel may be formed from Nickel in certain embodiments. This device provides a structure that overcomes problems identified in the art.

In another aspect, the invention is a method of forming a reinforced port in an axially extending tube defining a lumen. The method comprises inserting a construction mandrel within the lumen. This is followed by the step of cutting the tube parallel with the axis of the tube to remove a portion of the tube thereby forming an opening in the tube that exposes a portion of the lumen to an outside surface of the tube. Then, the construction mandrel is repositioned such that an end portion of the construction mandrel protrudes from the opening, a remaining portion of the construction mandrel remaining within the lumen. A stiffening mandrel is inserted within the lumen so that the stiffening mandrel spans across the opening from a distal side of the opening to a proximal side of the opening. Thereafter, a heat shrink cylinder is slid over the tube, to overlap with the opening and a portion of the construction mandrel protruding from the opening. The tube is covered with a pressure cylinder such that the shrink cylinder is entirely covered by the pressure cylinder. A heated fluid is introduced into the pressure cylinder to cause the shrink cylinder to shrink onto the tube and the construction mandrel, and to cause at least a portion of the lumen of the tube that is not occupied by the construction mandrel to collapse and become blocked The pressure cylinder is removed from covering the tube, and the construction mandrel is removed from the lumen of the tube, thereby leaving the opening to extend as a port from an outside surface of the tube into a portion of the lumen that was occupied by the construction mandrel before the construction mandrel was removed. In some embodiments, cutting the tube parallel with the axis of the tube includes using the construction mandrel as a guide for a blade to follow an axial path while cutting the tube. This provides an effective way of accomplishing a delicate and fragile operation on a small device.

In yet another aspect, the invention is a method of connecting a wire element to a tube defining a lumen. The method comprises providing a wire having a ball at a distal end of the wire. A circular collar is installed over the tube. A mandrel is inserted into the lumen of the tube. The ball on the wire end is inserted through the collar, whereby the distal end of the wire is held against an external surface of the tube. A tubular jacket is installed over the mandrel, the jacket having a first distal orifice configured to receive the mandrel, a central orifice configured to receive a liquid polymer, and a proximal orifice configured to receive the tube and the wire at a point of connection between the tube and the wire. A liquid polymer is poured into the central orifice. The liquid polymer is allowed to set, whereafter the mandrel is removed from the lumen. In some embodiments, installing a tubular jacket includes installing a tubular jacket made of a polymer. This provides a straightforward and effective way of accomplishing a difficult connection between delicate elements of a small device.

These and other advantages will become clearer when read in conjunction with the drawings and the detailed description of preferred embodiments.

BRIEF DESCRIPTION OF THE DRAWINGS

Many aspects of the present disclosure can be better understood with reference to the following drawings. The components in the drawings are not necessarily to scale. Instead, emphasis is placed on illustrating the principles of the present disclosure.

FIG. 4A is a schematic side view of an embodiment of the present technology, shown in an expanded condition for deployment.

FIG. 4B is a schematic side view of the embodiment of FIG. 4A, shown in a collapsed condition for delivery.

DETAILED DESCRIPTION OF THE PREFERRED EMBODIMENTS

Figure 1:
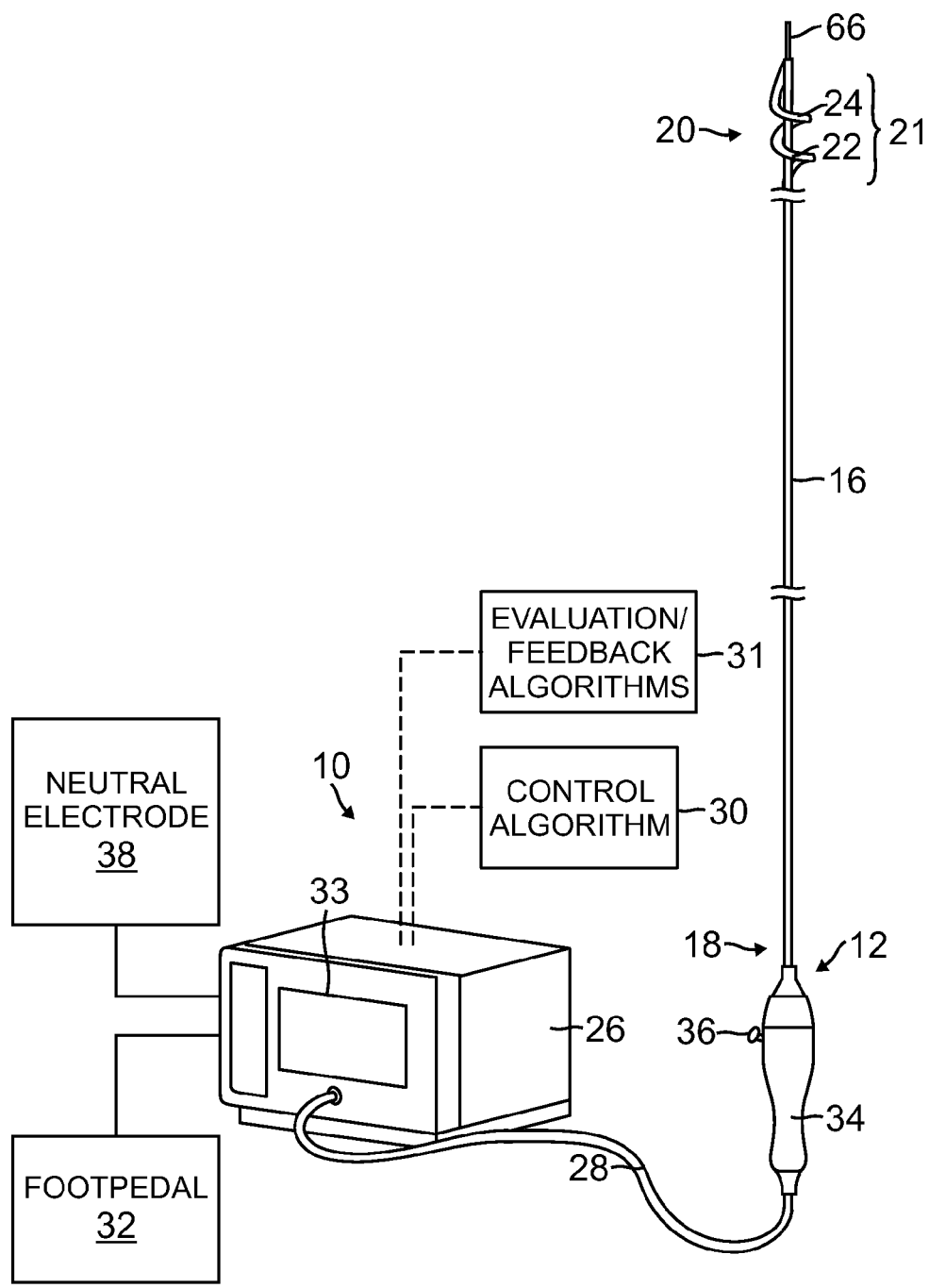
FIG. 1 illustrates an intravascular renal neuromodulation system configured in accordance with an embodiment of the present technology.

The applicants base the present application on the known discovery, as set forth above, that it may be desirable to perform a denervation treatment of the renal artery (renal denervation, or, renal neuromodulation) to positively affect a medical condition. In embodiments of the invention, such treatment may apply energy to zones of the renal artery normal to the artery wall. In some treatments, energy may be applied circumferentially. However, continuous circumferential lesions that extend continuously about a full 360° of the circumference of a cross-section normal to the body lumen or tissue in proximity to the body lumen may increase a risk of acute and/or late stenosis formation within the blood vessel. Therefore, embodiments described herein are directed to forming discrete lesions that do not form a circle in a single plane normal to the axis of the vessel.

Embodiments herein are configured to provide a non-continuous circumferential treatment that is performed over a lengthwise segment of the blood vessel (body lumen), as compared to a continuous circumferential treatment at a single normal cross-section or radial plane. Target structures such as nerves, including nerve fiber bundles, extending along the longitudinal dimension of the vessel are thus circumferentially affected, but not in continuous circumference about a single point of the vessel. Thus, the resulting lesion does not form a continuous circumferential lesion along any normal cross-section or radial plane of the vessel, but rather forms a helical lesion that may in some embodiments be a continuous helical lesion or in other embodiments a helical lesion with discontinuities along its path. This helical characteristic is believed to reduce the risk of acute or late stenosis formation within the blood vessel (body lumen) when compared with lesions that are formed to extend around a normal cross section of the vessel in single plane.

The non-continuous circumferential treatment is achieved in embodiments of the invention via apparatus positioned within a body lumen in proximity to target neural fibers for application of energy to the target neural fibers. The treatment may be induced, for example, via the application of electrical and/or electro-magnetic energy. Such treatment may be achieved, for example, via a thermal or non-thermal electric field, via a continuous or pulsed electric field, or via a stimulation electric field.

In some embodiments, methods and apparatus for real-time monitoring of the treatment and its effects on the target or support structures, and/or in non-target tissue, may be provided. Likewise, real-time monitoring of the energy delivery apparatus may be provided. Power or total energy delivered, impedance and/or the temperature, or other characteristics of the target or non-target tissue, or of the apparatus, additionally or alternatively may be monitored.

When utilizing an electric field to achieve desired circumferentially non-continuous treatment, the electric field parameters may be altered and combined in any combination, as desired. Such parameters can include, but are not limited to, frequency, voltage, power, field strength, pulse width, pulse duration, the shape of the pulse, the number of pulses and/or the interval between pulses (e.g., duty cycle).

When utilizing thermal or indirect thermal mechanisms to achieve the desired treatment, protective elements may be provided to protect the non-target tissue (such as the smooth muscle cells) from thermal damage during the thermally-induced non-continuous circumferential treatment. For example, when heating target nerves or support structures located about a vessel, protective cooling elements, such as convective cooling elements, may be provided to protect the non-target tissue. Likewise, when cooling target nerves or support structures, protective heating elements, such as convective heating elements, may be utilized to protect the non-target tissue. Thermal energy may be applied either directly or indirectly for a brief or a sustained period of time in order to achieve, for example, desired neuromodulation or denervation. Feedback, such as sensed temperature and/or impedance, along target or non-target tissue or along the apparatus, may be used to control and monitor delivery of the thermal energy.

The non-target tissue optionally may be protected during, e.g., the neuromodulation or denervation, by utilizing blood flow as a conductive and/or convective thermal sink that absorbs excess thermal energy (hot or cold). For example, when blood flow is not blocked, the circulating blood may provide a relatively constant temperature medium for removing the excess thermal energy from the non-target tissue during the procedure. The non-target tissue additionally or alternatively may be protected by focusing the thermal (or other) energy on the target or support structures, such that an intensity of the energy is insufficient to induce thermal damage in the non-target tissue distant from the target or support structures.

Embodiments of Catheter Apparatus

FIG. 1 illustrates a renal neuromodulation system 10 configured in accordance with an embodiment of the present technology. The system 10 includes an intravascular intraluminal device 12 operably coupled to an energy source or energy generator 26. In the embodiment shown in FIG. 1, the intraluminal device 12 (e.g., a catheter) includes an elongated shaft 16 having a proximal portion 18, a handle 34 at a proximal region of the proximal portion 18, and a distal portion 20 extending distally relative to the proximal portion 18. The intraluminal device 12 further includes a treatment assembly or treatment section 21 at the distal portion 20 of the shaft 16. As explained in further detail below, the treatment assembly 21 can include an array of two or more electrodes 24 configured to be delivered to a renal blood vessel (e.g., a renal artery) in a low-profile configuration. Upon delivery to the target treatment site within the renal blood vessel, the treatment assembly 21 is further configured to be deployed into an expanded state (e.g., a generally helical or spiral configuration) for delivering energy at the treatment site and providing therapeutically-effective electrically- and/or thermally-induced renal neuromodulation. In some embodiments, the treatment assembly 21 may be placed or transformed into the deployed state or arrangement via remote actuation, e.g., via an actuator 36, such as a knob, pin, or lever carried by the handle 34. In other embodiments, however, the treatment assembly 21 may be transformed between the delivery and deployed states using other suitable mechanisms or techniques.

The proximal end of the treatment assembly 21 is carried by or affixed to the distal portion of the elongated shaft 16. A distal end of the treatment assembly 21 may terminate the intraluminal device 12 with, for example, an atraumatic rounded tip or cap. Alternatively, the distal end of the treatment assembly 21 may be configured to engage another element of the system 10 or intraluminal device 12. For example, the distal end of the treatment assembly 21 may define a passageway for engaging a guide wire 66 for delivery of the intraluminal device using over-the-wire ("OTW") or rapid exchange ("RX") techniques.

The energy source or energy generator 26 (e.g., a RF energy generator) is configured to generate a selected form and magnitude of energy for delivery to the target treatment site via the electrodes 24. The energy generator 26 can be electrically coupled to the intraluminal device 12 via a cable 28. At least one supply wire (not shown) passes along the elongated shaft 16 or through a lumen in the elongated shaft 16 to the electrodes 24 and transmits the treatment energy to the electrodes 24. In some embodiments, each electrode 24 includes its own supply wire. In other embodiments, however, two or more electrodes 24 may be electrically coupled to the same supply wire. A control mechanism, such as foot pedal 32, may be connected (e.g., pneumatically connected or electrically connected) to the energy generator 26 to allow the operator to initiate, terminate and, optionally, adjust various operational characteristics of the generator, including, but not limited to, power delivery. The system 10 may also include a remote control device (not shown) that can be positioned in a sterile field and operably coupled to the electrodes 24. The remote control device is configured to allow for selectively turning on/off the electrodes. In other embodiments, the remote control device may be built into the handle assembly 34. The energy generator 26 can be configured to deliver the treatment energy via an automated control algorithm and/or under the control of the clinician. In addition, the energy generator 26 may include one or more evaluation or feedback algorithms to provide feedback to the clinician before, during, and/or after therapy.

Figure 2:
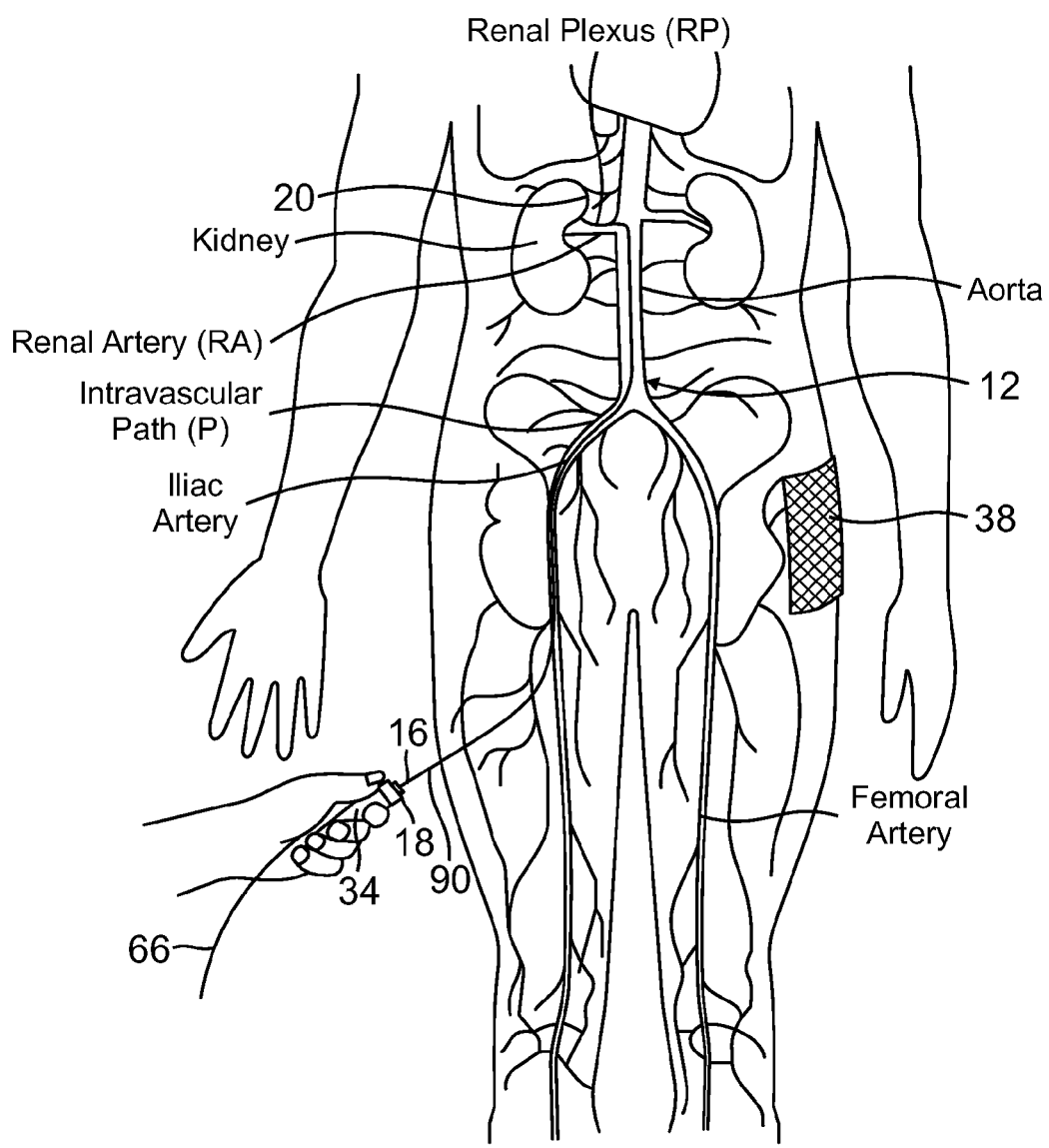
FIG. 2 illustrates modulating renal nerves with a multi-electrode catheter apparatus in accordance with an embodiment of the present technology.

In some embodiments, the system 10 may be configured to provide delivery of a monopolar electric field via the electrodes 24. In such embodiments, a neutral or dispersive electrode may be electrically connected to the energy generator 26 and attached to the exterior of the patient (as shown in FIG. 2). Additionally, one or more sensors (not shown), such as one or more temperature (e.g., thermocouple, thermistor, etc.), impedance, pressure, optical, flow, chemical or other sensors, may be located proximate to or within the electrodes 24 and connected to one or more supply wires (not shown). For example, a total of two supply wires may be included, in which both wires could transmit the signal from the sensor and one wire could serve dual purpose and also convey the energy to the electrodes 24. Alternatively, a different number of supply wires may be used to transmit energy to the electrodes 24.

The energy generator 26 may be part of a device or monitor that may include processing circuitry, such as a microprocessor, and a display. The processing circuitry may be configured to execute stored instructions relating to a control algorithm. The monitor may be configured to communicate with the intraluminal device 12 (e.g., via cable 28) to control power to the electrodes 24 and/or to obtain signals from the electrodes 24 or any associated sensors. The monitor may be configured to provide indications of power levels or sensor data, such as audio, visual or other indications, or may be configured to communicate the information to another device. For example, the energy generator 26 may also be configured to be operably coupled to a catheter lab screen or system for displaying treatment information.

FIG. 2 illustrates modulating renal nerves with an embodiment of the system 10. The intraluminal device 12 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion 18 of the shaft 16 is exposed externally of the patient. By manipulating the proximal portion 18 of the shaft 16 from outside the intravascular path P, the clinician may advance the shaft 16 through the sometimes tortuous intravascular path P and remotely manipulate the distal portion 20 of the shaft 16. Image guidance, e.g., computed tomography (CT), fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the intraluminal device 12 itself. After the treatment assembly 21 is adequately positioned in the renal artery RA, it can be radially expanded using the handle 34 or other suitable means until the electrodes 24 are in stable contact with the inner wall of the renal artery RA. The purposeful application of energy from the electrodes 24 is then applied to tissue to induce one or more desired neuromodulating effects on localized regions of the renal artery and adjacent regions of the renal plexus RP, which lay intimately within, adjacent to, or in close proximity to the adventitia of the renal artery RA. The purposeful application of the energy may achieve neuromodulation along all or at least a portion of the renal plexus RP.

The neuromodulating effects are generally a function of, at least in part, power, time, contact between the electrodes 24 and the vessel wall, and blood flow through the vessel. The neuromodulating effects may include denervation, thermal ablation, and non-ablative thermal alteration or damage (e.g., via sustained heating and/or resistive heating).

Figure 3A:
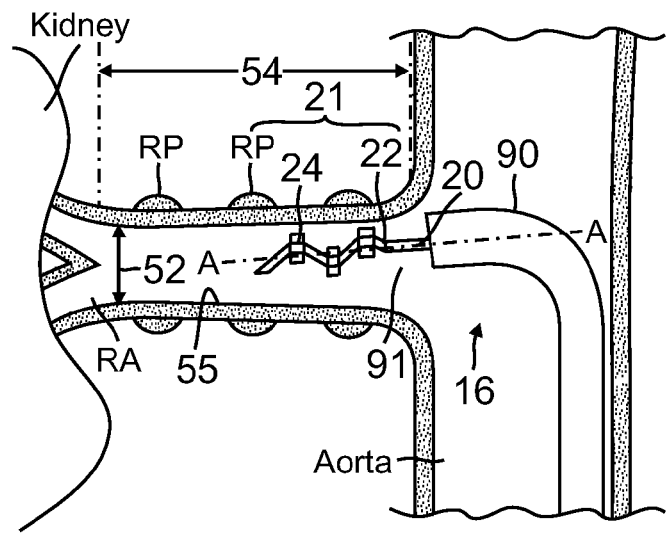
FIG. 3A is a view of a distal portion of a catheter shaft and a multi-electrode array in a delivery state (e.g., low-profile or collapsed configuration) within a renal artery used in conjunction with a guide catheter in accordance with an embodiment of the present technology.
Figure 3B:
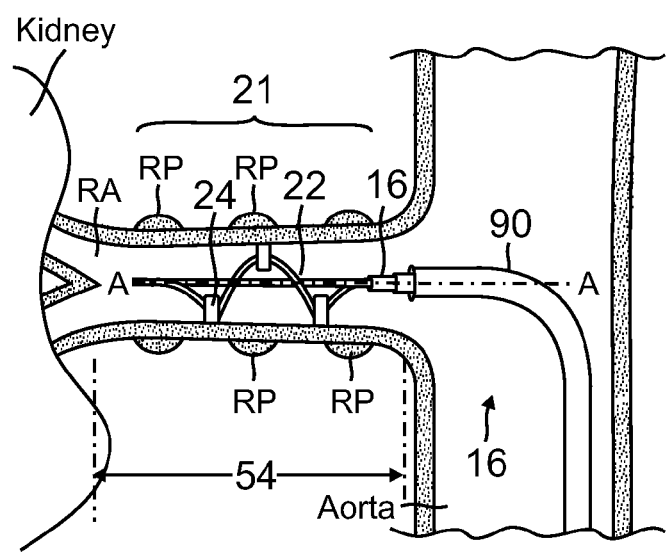
FIG. 3B is a view of the distal portion of the catheter shaft and the multi-electrode array of FIG. 3A in a deployed state (e.g., expanded configuration) within a renal artery in accordance with an embodiment of the technology.

Turning now to a more detailed description of certain embodiments, FIG. 3A is a schematic side view illustrating one embodiment of the distal portion of the shaft 16 and the treatment assembly 21 in a delivery state (e.g., low-profile or collapsed configuration) within a renal artery RA, and FIG. 3B illustrates the treatment assembly 21 in a deployed state (e.g., expanded or helical configuration) within the renal artery. Referring first to FIG. 3A, the collapsed or delivery arrangement of the treatment assembly 21 defines a low profile about the longitudinal axis A-A of the assembly such that a transverse dimension of the treatment assembly 21 is sufficiently small to define a clearance distance between an arterial wall 55 and the intraluminal device 12. The delivery state facilitates insertion and/or removal of the intraluminal device 12 and, if desired, repositioning of the treatment assembly 21 within the renal artery RA.

The distal portion 20 of the shaft 16 may flex in a substantial fashion to gain entrance into a respective left/right renal artery by following a path defined by a guide catheter, a guide wire, or a sheath. For example, the flexing of distal portion 20 may be imparted by the guide catheter 90, such as a renal guide catheter with a preformed bend near the distal end that directs the shaft 16 along a desired path, from the percutaneous insertion site to the renal artery RA. In another embodiment, the intraluminal device 12 may be directed to the treatment site within the renal artery RA by engaging and tracking a guide wire (e.g., guide wire 66 of FIG. 2) that is inserted into the renal artery RA and extends to the percutaneous access site. In operation, the guide wire is preferably first delivered into the renal artery RA and the elongated shaft 16 comprising a guide wire lumen is then passed over the guide wire into the renal artery RA.

After locating the treatment assembly 21 at the distal portion 20 of the shaft 16 in the renal artery RA, the treatment assembly 21 is transformed from its delivery state to its deployed state or deployed arrangement. The transformation may be initiated using an arrangement of device components as described herein with respect to the particular embodiments and their various modes of deployment. As described in greater detail below and in accordance with one or more embodiments of the present technology, the treatment assembly may be deployed by a deployment member, such as for example a pull- or tension-wire engaged with the shaping structure of the treatment assembly to apply a deforming or shaping force to the assembly to transform it into its deployed state.

Further manipulation of the shaping structure 22 and the electrodes 24 within the respective renal artery RA establishes apposition of the electrodes 24 against the tissue along an interior wall of the respective renal artery RA. For example, as shown in FIG. 3B, the treatment assembly 21 is expanded within the renal artery RA such that the electrodes 24 are in contact with the renal artery wall 55.

As best seen in FIG. 3B, in the deployed state, the treatment assembly 21 defines a substantially helical shaping structure 22 in contact with the renal artery wall 55 along a helical path. One advantage of this arrangement is that pressure from the shaping structure can be applied to a large range of radial directions without applying pressure to a circumference of the vessel. Thus, the helically-shaped treatment assembly 21 is configured to provide stable contact between the electrodes 24 and the artery wall 55 when the wall moves in any direction. Furthermore, pressure applied to the vessel wall 55 along a helical path is less likely to stretch or distend a circumference of a vessel that could thereby cause injury to the vessel tissue. Still another feature of the expanded shaping structure is that it may contact the vessel wall in a large range of radial directions and maintain a sufficiently open lumen in the vessel allowing blood to flow through the helix during therapy.

As best seen in FIG. 3B, in the deployed state, the shaping structure 22 defines a maximum axial length of the treatment assembly 21 that is approximately equal to or less than a renal artery length 54 of a main renal artery (i.e., a section of a renal artery proximal to a bifurcation). Because this length can vary from patient to patient, it is envisioned that the deployed helical-shaped shaping structure 22 may be fabricated in different sizes (e.g., with varying lengths and/or diameters) that may be appropriate for different patients. Referring to FIG. 3B, in the deployed state, the helical-shaped treatment assembly 21 provides for circumferentially discontinuous contact between the electrodes 24 and the inner wall 55 of the renal artery RA. That is, the helical path may comprise a partial arc (i.e., <360°), a complete arc (i.e., 360°) or a more than complete arc (i.e., >360°) along the inner wall of a vessel about the longitudinal axis of the vessel.

FIGS. 4A and 4B illustrate in more detail a distal portion of an intraluminal device 12 configured in accordance with embodiments of the present technology. More specifically, FIGS. 4A and 4B illustrate a treatment assembly 21 having an elongate shaping structure 22 helically wrapped about a deployment member 68 with a plurality of electrodes 24 disposed about the shaping structure 22.

In the illustrated embodiment, a distal region or portion of the shaping structure 22 terminates in an end piece (e.g., a conical or bullet-shaped tip 50) or, alternatively, a collar, shaft, or cap. The tip 50 can include a rounded distal portion to facilitate atraumatic insertion of the intraluminal device 12 into a renal artery. A proximal region or portion of the shaping structure 22 is coupled to and affixed to the elongated shaft 16 of the intraluminal device 12. The elongated shaft 16 defines a central passageway for passage of a deployment member 68. The deployment member 68 may be, for example, a solid wire made from a metal or polymer. The deployment member 68 extends from the elongated shaft 16 and is affixed to the distal region 22b of the shaping structure 22 at the tip 50. Moreover, the deployment member 68 slidably passes through the elongated shaft 16 to an actuator 36 in a handle assembly 34.

In this embodiment, the deployment member 68 is configured to move distally and proximally through the elongated shaft 16 so as to move the distal region of the shaping structure 22 accordingly. Distal and proximal movement of the distal region respectively lengthen and shorten the axial length of the helix of the shaping structure 22 so as to transform the treatment assembly 21 between a delivery (FIG. 4B) and deployed state (FIG. 4A) such that the electrodes 24 move a radial distance to engage the walls of the renal artery (not shown).

In one embodiment, deployment member 68 comprises a hollow tube defining an internal passage for a guide wire 66 to facilitate insertion of the treatment assembly 21 through an intravascular path to a renal artery. Accordingly, the intraluminal device 12 may be configured for an OTW or RX delivery. The deployment member 68 defines an internal lumen extending through the deployment member and composed of, for example, a polyimide tube with wall thickness less than about 0.003 inch (0.08 mm) (e.g., about 0.001 inch (0.02 mm)) and a lumen with a diameter of less than about 0.015 inch (0.38 mm) (e.g., about 0.014 inch (0.36 mm)). In addition to engaging and tracking along the guide wire 66, the device 12 transforms the configuration of the treatment assembly 21 between the delivery state and the deployed state.

Figure 5A:
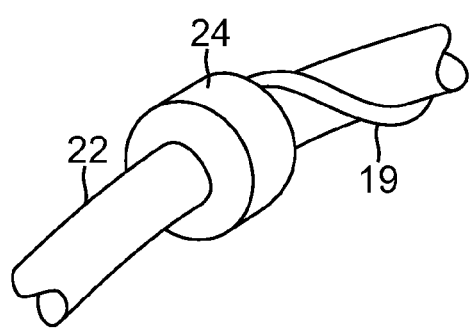
FIG. 5A is a schematic perspective view of an electrode positioned on a shaping structure.
Figure 5B:
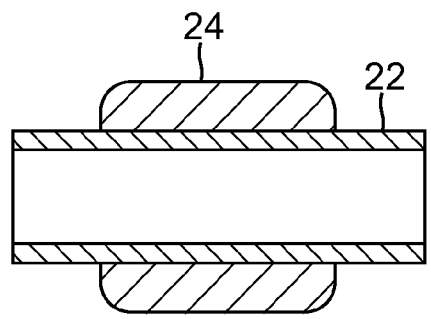
FIG. 5B is a sectional view of the view shown in FIG. 5A.
Figure 5C:
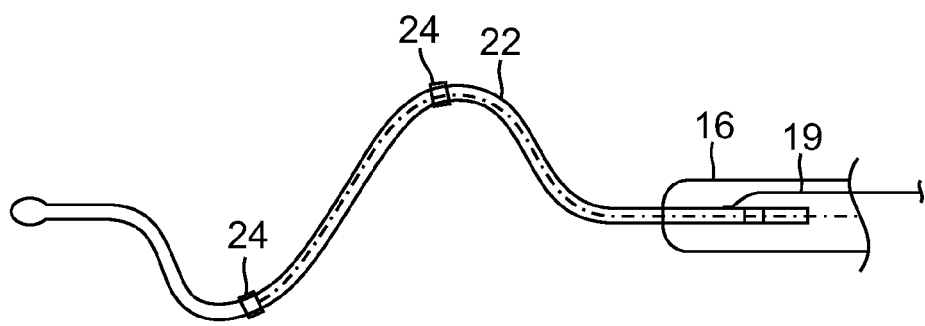
FIG. 5C is a schematic view of an embodiment showing electrical lead line connecting to an electrode.

It should be understood that the embodiments provided herein may be used in conjunction with one or more electrodes 24. As described in greater detail below, the deployed helically-shaped structure carrying the electrodes 24 is configured to provide a therapeutic energy delivery to the renal artery without any repositioning. Illustrative embodiments of the electrodes 24 are shown in FIGS. 5A-5C. The electrodes 24 associated with the shaping structure 22 may be separate elements or may be an integral part of the shaping structure 22. In some patients, it may be desirable to use the electrode(s) 24 to create a single lesion or multiple focal lesions that are spaced around the circumference of the renal artery. A single focal lesion with desired longitudinal and/or circumferential dimensions, one or more full-circle lesions, multiple circumferentially spaced focal lesions at a common longitudinal position, spiral-shaped lesions, interrupted spiral lesions, generally linear lesions, and/or multiple longitudinally spaced discrete focal lesions at a common circumferential position alternatively or additionally may be created. In still further embodiments, the electrodes 24 may be used to create lesions having a variety of other geometric shapes or patterns.

Depending on the size, shape, and number of the electrodes 24, the formed lesions may be spaced apart around the circumference of the renal artery and the same formed lesions also may be spaced apart along the longitudinal axis of the renal artery. In particular embodiments, it is desirable for each formed lesion to cover at least 10% of the vessel circumference to increase the probability of affecting the renal plexus. Furthermore, to achieve denervation of the kidney, it is considered desirable for the formed lesion pattern, as viewed from a proximal or distal end of the vessel, to extend at least approximately all the way around the circumference of the renal artery. In other words, each formed lesion covers an arc of the circumference, and each of the lesions, as viewed from an end of the vessel, abut or overlap adjacent or other lesions in the pattern to create either an actual circumferential lesion or a virtually circumferential lesion. The formed lesions defining an actual circumferential lesion lie in a single plane perpendicular to a longitudinal axis of the renal artery. A virtually circumferential lesion is defined by multiple lesions that may not all lie in a single perpendicular plane, although more than one lesion of the pattern can be so formed. At least one of the formed lesions comprising the virtually circumferential lesion is axially spaced apart from other lesions. In a non-limiting example, a virtually circumferential lesion can comprise six lesions created in a single helical pattern along the renal artery such that each lesion spans an arc extending along at least one sixth of the vessel circumference such that the resulting pattern of lesions completely encompasses the vessel circumference when viewed from an end of the vessel. In other examples, however, a virtually circumferential lesion can comprise a different number of lesions. It is also desirable that each lesion be sufficiently deep to penetrate into and beyond the adventitia to thereby affect the renal plexus. However, lesions that are too deep (e.g., >5 mm) run the risk of interfering with non-target tissue and tissue structures (e.g., a renal vein) so a controlled depth of energy treatment is also desirable.

Referring back to FIG. 3B, the individual electrodes 24 are connected to energy generator 26 (FIG. 1) and are sized and configured to contact an internal wall of the renal artery. In the illustrated embodiment, the electrode 24 may be operated in a monopolar or unipolar mode. In this arrangement, a return path for the applied RF electric field is established, e.g., by an external dispersive electrode (shown as element 38 in FIGS. 1 and 2), also called an indifferent electrode or neutral electrode. The monopolar application of RF electric field energy serves to ohmically or resistively heat tissue in the vicinity of the electrode. The application of the RF electrical field thermally injures tissue. The treatment objective is to thermally induce neuromodulation (e.g., necrosis, thermal alteration or ablation) in the targeted neural fibers. The thermal injury forms a lesion in the vessel wall. Alternatively, a RF electrical field may be delivered with an oscillating or pulsed intensity that does not thermally injure the tissue whereby neuromodulation in the targeted nerves is accomplished by electrical modification of the nerve signals.

The active surface area of the electrode 24 is defined as the energy transmitting area of the element 24 that may be placed in intimate contact against tissue. Too much contact area between the electrode and the vessel wall may create unduly high temperatures at or around the interface between the tissue and the electrode, thereby creating excessive heat generation at this interface. This excessive heat may create a lesion that is circumferentially too large. This may also lead to undesirable thermal application to the vessel wall. In some instances, too much contact can also lead to small, shallow lesions. Too little contact between the electrode and the vessel wall may result in superficial heating of the vessel wall, thereby creating a lesion that is too small (e.g., <10% of vessel circumference) and/or too shallow.

In certain embodiments, the shaping structure 22 may be formed of an electrically conductive material. For example, the shaping structure 22 may be made from nitinol wire, cable, or tube. As shown in FIG. 5C, wire leads 19 may connect the shaping structure 22 to energy generator 26. The shaping structure 22 forms a contact region with the renal artery wall and acts as the electrode 24. In this configuration, the shaping structure 22 is capable of producing a continuous helical lesion. A shaping structure 22 that is configured to be an electrode 24 may optionally comprise sensors positioned on, in, and/or proximate to the shaping structure 22 and may be electrically connected to supply wires.

In other embodiments, the electrically conductive shaping structure 22 is insulated at least in part. That is, the conductive shaping structure is partially covered with an electrically insulating material and the uncovered portions of the shaping structure 22 serve as one or more conductive electrodes 24. The electrodes 24 may be any size, shape, or number, and may be positioned relative to one another as provided herein.

Electrode 24 may be configured to deliver thermal energy, i.e., to heat up and conduct thermal energy to tissue. For example, electrodes may be an electrically resistive element such as a thermistor or a coil made from electrically resistive wire so that when electrical current is passed through the electrode heat is produced. An electrically resistive wire may be for example an alloy such as nickel-chromium with a diameter for example between 48 and 30 AWG. The resistive wire may be electrically insulated for example with polyimide enamel.

Figure 6A:
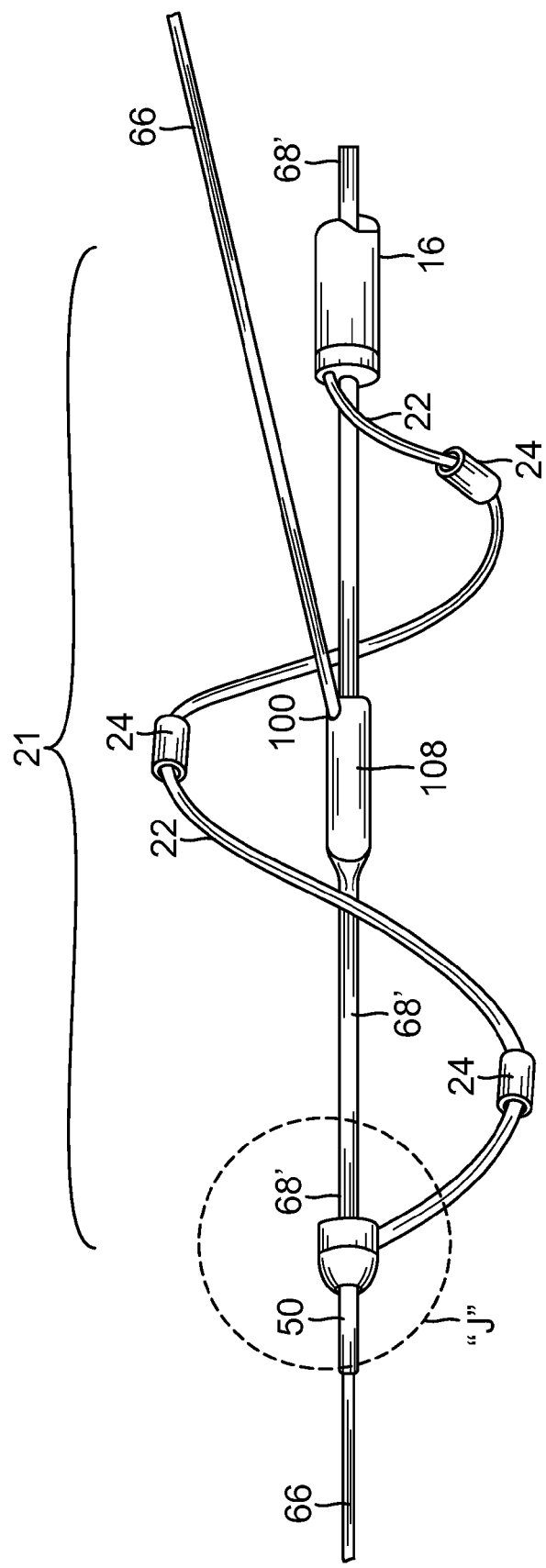
FIG. 6A is a schematic side view of a catheter portion having features of the invention, shown in an expanded condition for deployment.
Figure 6B:
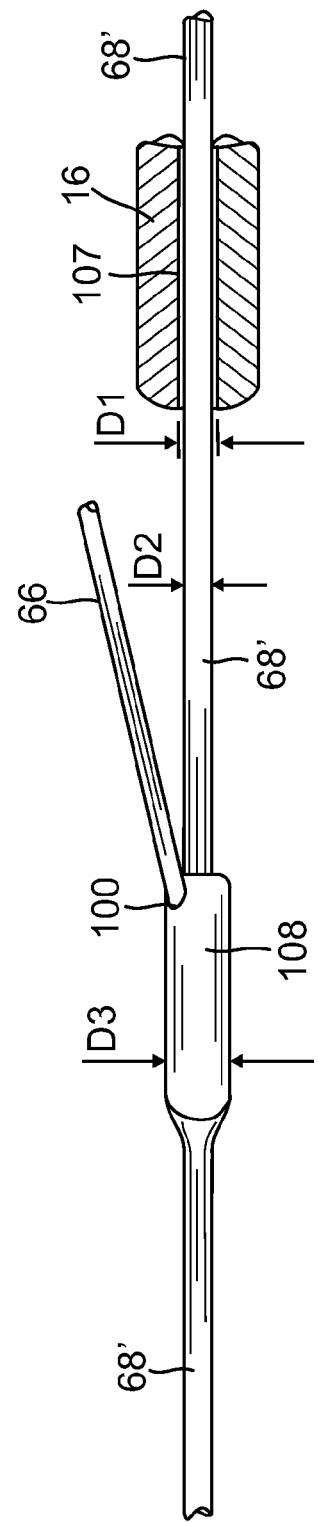
FIG. 6B is a schematic side view, in partial cutaway, of the view shown in FIG. 6A, showing a more detailed view.
Figure 6C:
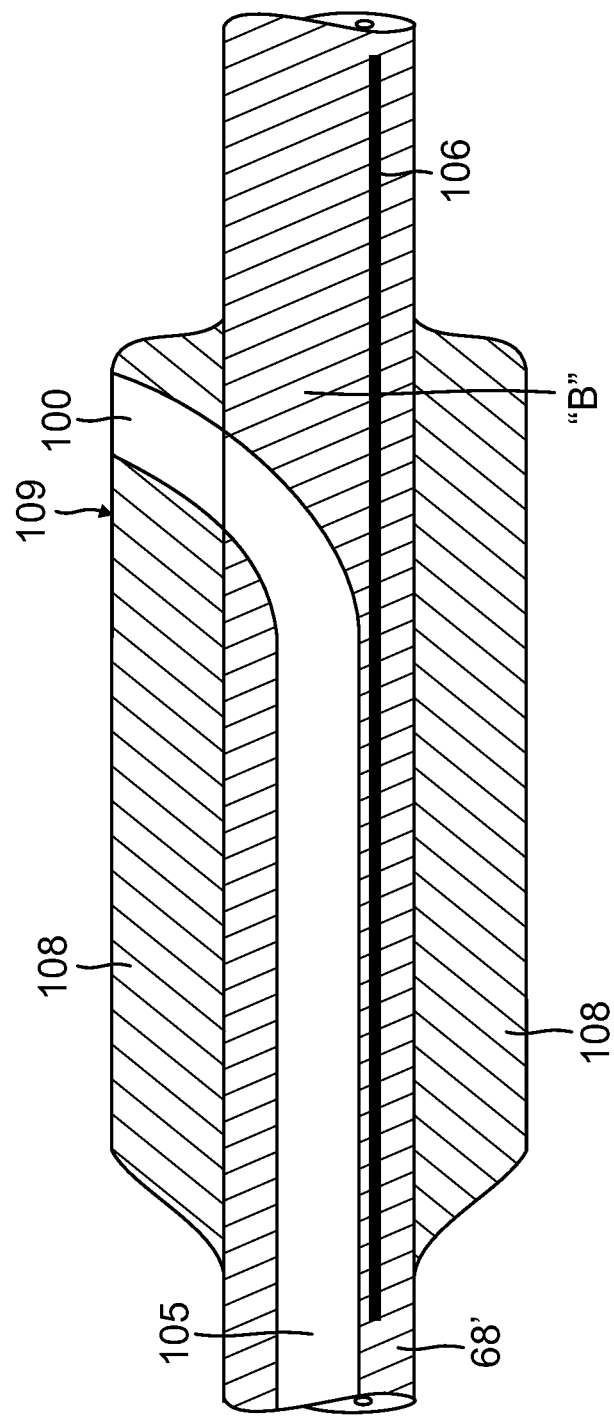
FIG. 6C is a sectional view taken through a portion of the elements shown in FIG. 6A and FIG. 6B.

Turning now to an embodiment of the invention exemplified in FIG. 6A-6C, this embodiment discloses that a rapid exchange type catheter is contemplated wherein the catheter is not configured to receive a guidewire in a lumen extending all the way along the length of the catheter such as in a so-called "over the wire" or "OTW" catheter. Rather, the embodiment is configured to provide a "rapid exchange" or "RX" type catheter with an exit port 100 for the guidewire 66 to emerge from the catheter a few centimeters proximal of the distal tip 50 of the catheter. This embodiment discloses a novel and useful structural arrangement and method for locating the exit port, and also a method for fabricating the exit port and associated helical shaping structure 22.

First, a feature of the guidewire exit port of this embodiment of the invention is its location in a novel and advantageous location on the catheter. In this embodiment of the invention, an exit port 100 is located in the deployment member 68'. This has a number of advantageous characteristics. By locating the exit port on the deployment member 68' avoids the guidewire being in a structural association with the elongated shaft 16 which carries a number of electrical leads. This in turn avoids the danger of contact between the guidewire and the electrical leads. Further, by not locating the exit port on the elongated shaft 16, the elongated shaft has a more slender profile. By locating the exit shaft on the deployment member 68' the tip 50 maintains a soft texture that is required for navigating the tortuous anatomy of the patient.

The method by which the exit port is fabricated, in one embodiment of the invention, will now be described with reference to FIGS. 7-13A. A suitable length of deployment member 68' is selected. It will be appreciated that the deployment member 68' will eventually extend all the way from the proximal end of the catheter (where it is connected to a known means for pulling and pushing the deployment member 68') to the distal end of the catheter where it terminates in the distal tip 50. The deployment member of this embodiment is initially configured to define a lumen 105 (seen in FIGS. 12A and 12B) extending all the way along its length of sufficient dimension to receive a guidewire. (In the embodiment shown in FIG. 4, the same deployment member may be used, but in the present embodiment, an exit port will be introduced as described herein.) Again, in the embodiment shown in FIG. 6A-6C, and as with the embodiment of FIG. 4, the deployment member is configured to slide within a lumen 107 of the catheter shaft 16.

Figure 7A:
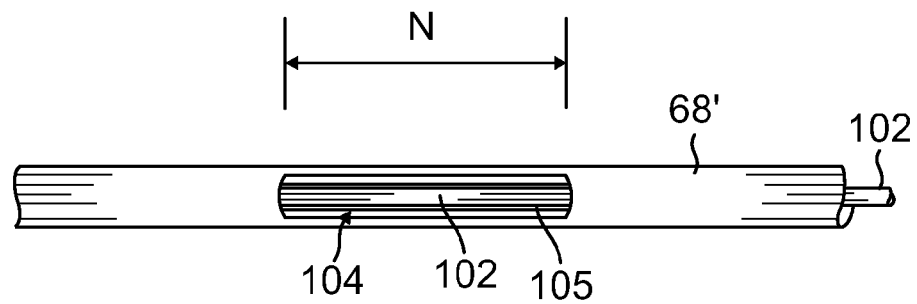
FIG. 7A is a top view of a portion of a catheter, showing a step in the manufacture of a catheter portion.
Figure 7B:
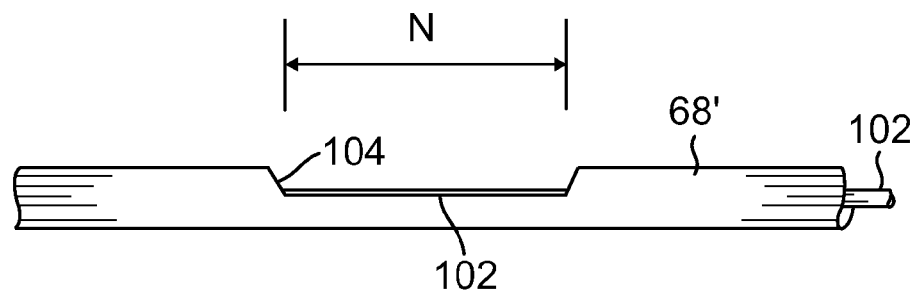
FIG. 7B is a side view of the catheter portion shown in FIG. 7A.
Figure 8:
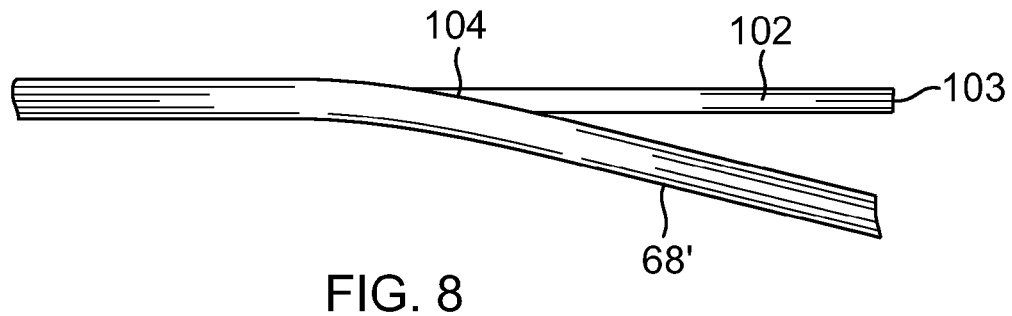
FIG. 8 is a view of the catheter portion shown in FIG. 7B, at a later stage of manufacture.

With reference to FIGS. 7A-7B, an initial step in the method of fabrication is to insert a construction mandrel 102 into the lumen 105 of the deployment member 68'. Once the mandrel is in position, a short opening 104 of length "N" is shaved into the deployment member using a sharp blade. The mandrel 102 prevents the blade from slicing through the deployment member, and forces the blade to run parallel with the axis in a horizontal plane just above the lumen. A suitable length of "N" is between 3 mm and 5 mm. The location of the opening 104 along the length of the deployment member is selected to be a few centimeters from the distal tip of the deployment member, so that the opening will eventually be located in the middle of the shaping structure 22 when the shaping structure is collapsed.

Once the opening 104 has been sliced into the deployment member 68', the construction mandrel 102 is withdrawn distally until its proximal tip 103 emerges from the opening 104. The proximal tip of the construction mandrel is then advanced proximally until a few centimeters of the construction mandrel extend outside the lumen of the deployment member, while the rest of the mandrel extends within the lumen of the deployment member, as exemplified in FIG. 8.

Figure 9:
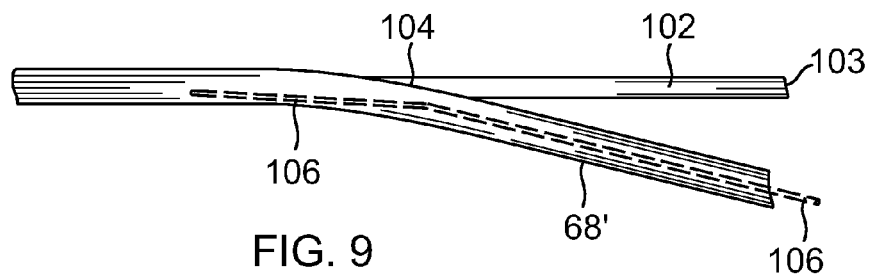
FIG. 9 is a view of the catheter portion shown in FIG. 8, at a later stage of manufacture.

At this stage, a stiffening mandrel 106, preferably made from a metal such as nickel or titanium and sized to fit comfortably within the lumen 105 of the deployment member 68' is inserted into the lumen from the distal end of the deployment member and extended proximally until it extends beyond the opening 104, but still confined within the lumen, as exemplified in FIG. 9. (The stiffening mandrel is shown dotted line to indicate its presence inside the lumen 105.) The stiffening mandrel is sized to provide the deployment member 68' with sufficient strength at the location of the opening to sustain a compression load when the deployment member is used in its "push" function to restore the shaping element to its collapsed configuration.

Figure 10:
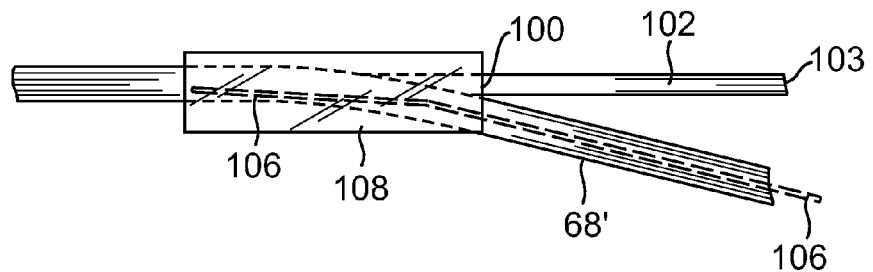
FIG. 10 is a view of the catheter portion shown in FIG. 9, at a yet later stage of manufacture.

Next, as seen in FIG. 10, a short heat shrink tube 108 (is slid down over the deployment member 68' from the distal end, until it covers the opening 104. As may be seen in FIG. 10, the construction mandrel 102 is left in its position, extending proximally from the exit port 104. The shrink tube 108, is made from a known polymer (nylon or polyolefin) designed to shrink dramatically in diameter but not length when it is heated by a fluid which may be either a gas or a liquid.

Figure 11:
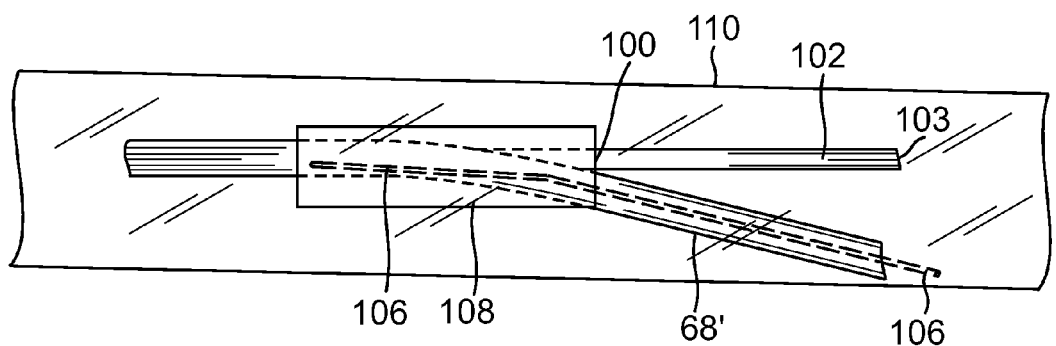
FIG. 11 is a view of the catheter portion shown in FIG. 10, at a later stage of manufacture.

Then, the portion of the deployment member 68' that includes the opening and shrink tube is inserted within a larger diameter pressure tube 110, as exemplified in FIG. 11. The pressure tube is preferably about 50 mm in length. Heated fluid under pressure is introduced into the pressure tube. The heated fluid firstly causes the shrink tube 104 to shrink onto the deployment member 68' and the construction mandrel 102. The shrink tube is positioned to neatly seal off most of the opening 104, but to leave a small "notch" or exit port 100 at the location where the construction mandrel emerges. The heated fluid secondly causes that proximal portion of the lumen of the deployment member 68' which is not occupied by the construction mandrel 102 to tend to collapse onto itself, the deployment member being formed from a polymer such as polyimide. This effectively blocks the passage of the lumen 105 just proximal of the opening 104. It will be appreciated that this collapse takes place only over the extent of the deployment member that was covered by the pressure tube 110. This has the beneficial result of blocking the passage of the original lumen 105 of the deployment member for a short distance proximal of the opening 104, with the result that a guidewire that is inserted from the distal end of the deployment member lumen 105 cannot advance all the way down the lumen but will be forced out of the deployment member 68' at the location of the exit port 100. Furthermore, the action of the heated fluid under pressure has the effect of locking the deployment member 68' onto the stiffening mandrel 106 in the region proximal of the opening 104 where the lumen has collapsed, and also in the region distal of the port 100 because the pressurized fluid compresses the construction mandrel against the stiffening mandrel, and forces the stiffening mandrel to become embedded in the internal wall of the lumen. Thus, when the stiffening mandrel 106 is eventually placed under compression in the vicinity of the opening 104, the stiffening mandrel is held against buckling by the deployment member 68'.

Figure 12A:
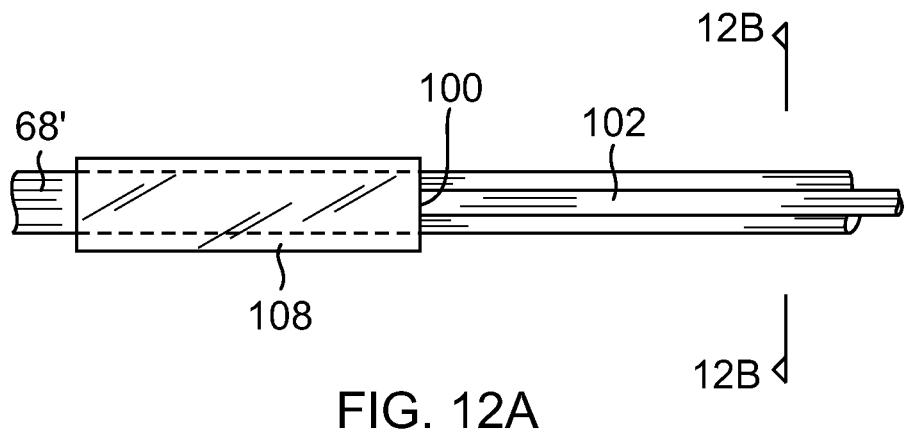
FIG. 12A is a view of the catheter portion shown in FIG. 11, at a later stage of manufacture.
Figure 13A:
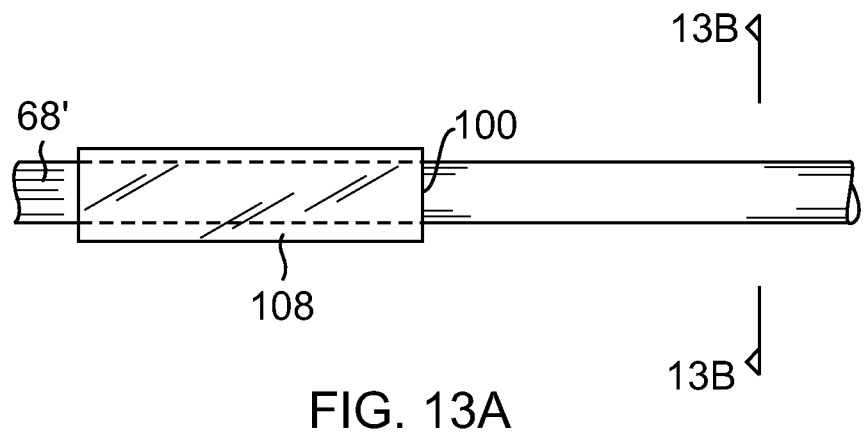
FIG. 13A is a view of the catheter portion shown in FIG. 12A, showing a step in the manufacture of the catheter portion.

Next, the pressure tube 110 is removed from its position surrounding the deployment member 68'. FIG. 12A. Then, the construction mandrel is slidingly removed from the lumen of the deployment member. FIG. 13A and FIG. 6C schematically exemplify the resulting structure. What is left is the distal end of the deployment member 68', having a conveniently shaped exit port 100 located at a position on the deployment member that will eventually be located about half way along the length of an exposed portion of the deployment member, as may be envisaged with reference to FIG. 6A. The lumen of the distal most portion of the deployment member, which housed the construction mandrel during the pressurized heating process, remains fully open to receive a distal end of a guidewire, which will then be passed proximally down the lumen of the deployment member, to emerge at the port 100, from where it travels proximally outside the catheter as seen in FIG. 6A.

The port 100 of the present invention has a number of advantages. As best seen in FIG. 6C, the deployment member 68' defines a neat opening 100 or port extending between the lumen 105 of the deployment member and an exterior surface 109 of the deployment member. The lumen 105 is blocked in the region proximal of the port 100, as indicated by the region marked with the letter "B" in FIG. 6C, thereby providing a convenient ramp for a guidewire being advanced proximally down the lumen 105 to be deflected out of the port 100. The deployment member in the region of the port 100 is reinforced by the shrink tube 108 which has been shrunk into place and is also reinforced against buckling by the stiffening mandrel 106. Because the deployment member in this region is surrounded by material derived from the shrink tube 108, this causes the outside diameter D3 of the deployment member in the vicinity of the shrink tube 108 and the port 100 to be substantially larger than the diameter D2 of the rest of the deployment member 68' in a portion that extends outside the catheter lumen. Notably, the diameter D3 of the shrink tube is configured to be greater than the internal diameter D1 of the lumen 107 in which a portion of the deployment member slides. This feature has the advantage of providing a blocking element, which prevents the deployment member from being withdrawn too far into the lumen 107 of the elongated shaft 16 as may be envisaged with reference to FIG. 6B. Otherwise, if the deployment member were extended too far into the lumen 107 of the elongated shaft 16, there would be a danger that (a) the helical shaping element 22 might form too large a diameter and apply too great a force between the electrodes 24 and the vascular wall, and (b) the guidewire 66 may be damaged: The present invention avoids this result.

Turning now to another aspect of the invention, a novel system and method is described, in conjunction with FIGS. 6, 14-17, for connecting a shaping structure 22 to a deployment member 68'. As can be seen in FIG. 6A, the shaping structure 22 that carries electrodes 24 is connected to a distal end of the deployment member 68' at the location identified as "J".

Figure 14:
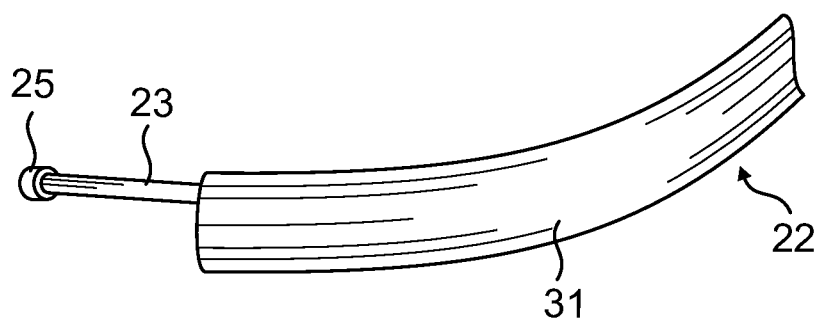
FIG. 14 is a side view of a catheter portion, at an early stage of manufacture.
Figure 12B:
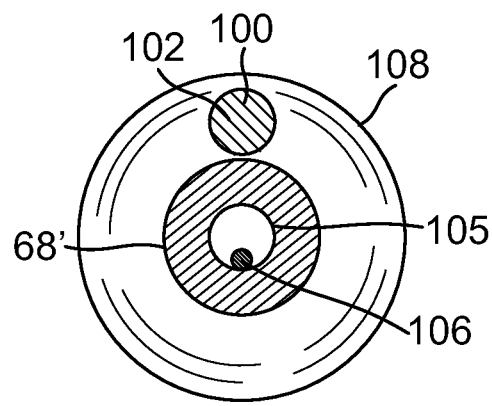
FIG. 12B is an end view of the catheter portion shown in FIG. 12A.
Figure 13B:
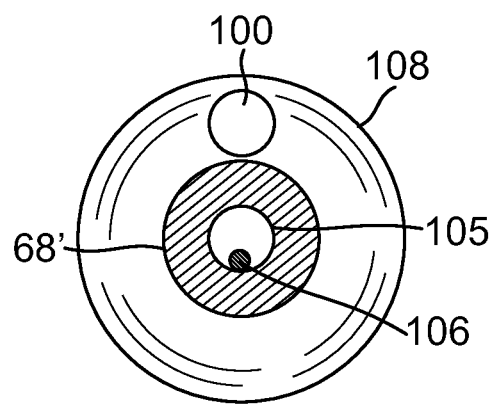
FIG. 13B is an end view of the catheter portion shown in FIG. 13A.

In some embodiments of the invention, this connection may be achieved as follows in order to overcome difficulties found in the prior art. The components of the shaping structure 22 are prepared by installing an insulating jacket 31 over a nitinol wire 23, as seen in FIG. 14. The insulating jacket is configured to act to separate the electrodes 24 and lead lines from the nitinol wire. At the distal tip of the nitinol wire 23 a ball 25 is fashioned for temporarily securing the wire 23 as will be described herein.

Figure 15:
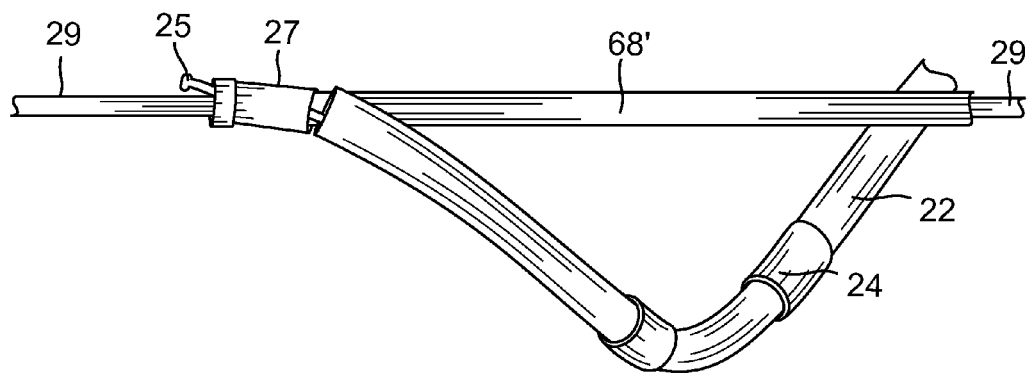
FIG. 15 is a view of the catheter portion shown in FIG. 14, at a later stage of manufacture.

With reference to FIG. 15, a collar 27, preferably made of a polymer compound, is slipped over the deployment member 68'. A mandrel 29 is inserted into the lumen of the deployment member. Then, the end of the nitinol wire bearing the ball 25 is slipped under the collar 27 as seen in FIG. 15, so that the nitinol wire becomes trapped against the external surface of the deployment member 68'. This is advantageous because it assists the assembler in the next stage of the assembly, freeing hands to perform the next task.

Figure 16:
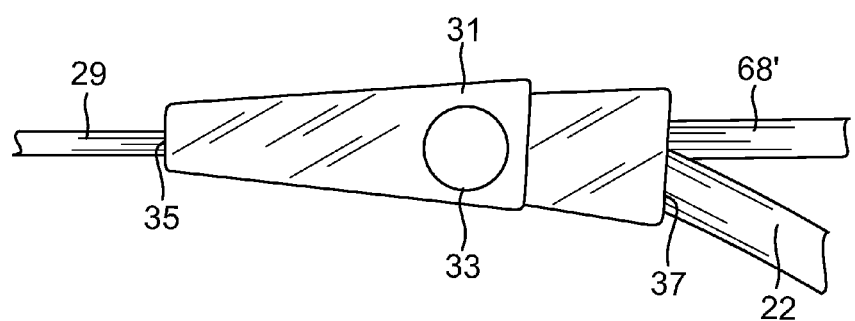
FIG. 16 is a view of the catheter portion shown in FIG. 15, at a later stage of manufacture.

At this stage, a custom shaped jacket 31 is slipped down over the mandrel, and thence over the contact point between the deployment member 68' and the shaping structure 22, as seen in FIG. 16. The custom shaped jacket is essentially a tapered tube with three orifices, a central orifice 33 configured for receiving a locking polymer that will be poured into the interior recess of the jacket 31. A proximal orifice 37 through which the mandrel 29 is first inserted, and then followed by the contact region between the deployment member 68' and the shaping structure 22. Finally, a distal orifice 35 is provided, through which the mandrel 29 extends distally when the jacket is in its final position. Once in its final position, a liquid polymer is poured in through the central orifice 33 until the unoccupied space inside the jacket is filled up with the polymer. The liquid polymer forms a strong bond with the polymer forming the jacket, and after a while during which heat may be applied, the liquid polymer solidifies, leaving a well protected connection between the shaping element and the deployment member. The connection is sufficiently pliable that the shaping element may be deployed and collapsed without any fracture to the joint. Thus, a novel and useful connection is formed between two elements of the invention that requires a minimum amount of preparation, and which is easy to assemble by hand.

Although preferred illustrative variations of the present invention are described above, it will be apparent to those skilled in the art that various changes and modifications may be made thereto without departing from the invention. For example, it will be appreciated that combinations of the features of different embodiments may be combined to form another embodiment. Furthermore, although in the described embodiments the apparatus and methods are for conducting in a blood vessel, it should be understood that treatment alternatively may be conducted in other body lumens. It is intended in the appended claims to cover all such changes and modifications that fall within the true spirit and scope of the invention.

We claim:

1. A catheter apparatus for treatment of a patient comprising:
    an elongate shaft defining a first lumen with a first internal diameter;
    a shaping structure having a distal end and a proximal end and a length therebetween, the shaping structure being moveable between a delivery state having a first helical shape, and a deployed state having a second helical shape;
    at least one electrode that is carried by the shaping structure;
    a deployment member having a second lumen, a first portion of the deployment member being positioned within the first lumen and having a second external diameter sized to enable the deployment member to slide within the first lumen, the deployment member being coupled to the distal end of the shaping structure at a coupling and being configured such that distal axial movement of the deployment member places the shaping structure in the delivery state, and proximal axial movement of the deployment member places the shaping structure in the deployed state;
    wherein a second portion of the deployment member is positioned outside the first lumen and defines a port configured to extend between the second lumen and an exterior surface of the deployment member; wherein the port is located between the coupling of the deployment member with the distal end of the shaping structure and the first lumen; and further
    wherein the deployment member includes reinforcing material around the port, the reinforcing material having a third external diameter that is larger than the first internal diameter of the elongate shaft such that, during proximal axial movement of the deployment member within the first lumen, the reinforcing material cannot enter into the first lumen but acts as a block against further proximal movement of the deployment member.

2. The catheter apparatus of claim 1, wherein the second lumen is blocked proximal to the port.

3. The catheter apparatus of claim 2 wherein a guidewire extends along the second lumen from a distal end of the deployment member, the guidewire emerging from the second lumen to the exterior surface of the deployment member via the port.

4. The catheter apparatus of claim 1, wherein a stiffening mandrel is located within the deployment member, the stiffening mandrel extending from a location proximal of the port to a location distal of the port.

5. The catheter apparatus of claim 4, wherein the stiffening mandrel is formed from nickel.

\* \* \* \* \*